United States Patent [19]

Haga

[11] Patent Number: 5,233,203
[45] Date of Patent: Aug. 3, 1993

[54] APPARATUS FOR DETECTING SURFACE DEFECTS ON A SEMICONDUCTOR WAFER

[75] Inventor: Sachiko Haga, Yamagata, Japan

[73] Assignee: NEC Corporation, Tokyo, Japan

[21] Appl. No.: 833,096

[22] Filed: Feb. 10, 1992

[30] Foreign Application Priority Data

Feb. 8, 1991 [JP] Japan ................... 3-5005[U]

[51] Int. Cl.[5] ............................................. G01N 21/88
[52] U.S. Cl. ..................................... 250/571; 356/237
[58] Field of Search ............... 250/571, 572, 562, 563; 356/338, 339, 237, 430

[56] References Cited

U.S. PATENT DOCUMENTS

| | | | |
|---|---|---|---|
| 4,740,708 | 4/1988 | Batchelder | 250/572 |
| 4,943,732 | 7/1990 | Economou | 250/572 |
| 5,127,726 | 7/1992 | Moran | 250/572 |

FOREIGN PATENT DOCUMENTS 0127652  6/1987  Japan ..................... 250/572

Primary Examiner—David C. Nelms
Assistant Examiner—John R. Lee

[57] ABSTRACT

An apparatus for detecting surface defects of a wafer includes a rotary unit rotatably attached to a vertical surface of a Z-X unit provided on a vertical surface of an L-shaped base and rotated with a vertically oriented semiconductor wafer held thereon by an attractive force of negative pressure created inside the rotary unit by evacuation of the air therein. An optical microscope is provided, which has its optical axis normal to the vertical surface of the wafer. The field of the microscope is moved smoothly along a radius direction of the wafer including the edge and the center of the wafer by the Z-X unit. At the same time, the wafer surface is illuminated by a spot laser beam, and blown by clean air ejected from a nozzle. The entire wafer surface is optically inspected by the optical microscope to receive reflected light which is detected by a photomultiplier for detecting deflects, such as particles, on the wafer surface.

8 Claims, 1 Drawing Sheet

APPARATUS FOR DETECTING SURFACE DEFECTS ON A SEMICONDUCTOR WAFER

BACKGROUND OF THE INVENTION

Field of the Invention

This invention relates to an apparatus for detecting minute particles on a semiconductor wafer surface.

Description of the Related Arts

Minute foreign particles deposited on a wafer surface lower the yield of semiconductor devices manufactured from a wafer. Therefore, to improve the yield, it is very important to check the wafer surfaces to detect minute particles.

In the conventional apparatus for detecting minute particles on a wafer surface, a wafer is mounted on a horizontal base surface of X-Y-$\theta$ stage so that the wafer may be moved and/or rotated in a horizontal plane of the stage while the wafer is inspected to detect minute particles with an optical microscope whose optical axis is perpendicular to the wafer surface. The optical microscope is connected to a photosensor for sensing the particles. This sensor signal is sent to a signal processor which determines particle size and number.

As above-mentioned, the wafer surface is moved horizontally. During its inspection, dust existing in the surroundings of the apparatus and released from an operator may easily fall on the wafer surface. Such deposition of minute particles is likely to occur particularly when the objective lens is changed or the optical path is switched by change lever for visual inspection.

SUMMARY OF THE INVENTION

A primary object of the present invention is to provide an apparatus for detecting minute particles which can eliminating such drawback as mentioned above inherent in the prior art apparatus, by preventing minute particles from being fallen on a wafer surface during the inspection.

To attain the object of the present invention, there is provided an apparatus for detecting minute particles, comprising: a rotary stage for holding a wafer whose surface is maintained vertically; a spot light scanner for scanning the wafer surface; an optical microscope having its optical axis of the objective lens directed normal to the vertical wafer surface, for receiving light reflected from the surface; a light sensor attached to the microscope for sensing the light reflected from the wafer surface; and a nozzle for ejecting clean air onto the wafer surface to blow off the particles.

With this construction, it is possible to prevent deposition of minute particles such as dust floating in ambient air onto the wafer surface during inspection.

In order to enhance sensitivity and hence accuracy of minute particle detection, the spot light scanner is preferably a spot laser beam scanner, and the light sensor is preferably a photomultiplier.

The rotary stage is preferably held for rotation on Z-X axis stages which are attached on a substantially L-shaped surface of a base, and the optical microscope is preferably mounted on an vertical support extending from a horizontal surface of the base. This arrangement permits construction of a compact scanning mechanism for the apparatus for inspecting wafer surface.

Further, the rotary stage is preferably constructed in the form of a hollow cylinder with one end thereof closed by a wall formed with a plurality of suction holes and the other end in frictional contact with the vertical surface of the Z-axis stage, the air trapped in the hollow cylinder being extracted through an exhaust duct. This arrangement permits suction of the wafer and simple stable mounting of the wafer on the rotary stage.

The rotary stage is preferably rotated at a high speed and is moved in the vertical direction by the Z-axis stage during the inspection of the wafer surface. This permits not only reduction of the inspection time but also detection of any microscopic particles in the order of a micron by controlling the vertical moving speed by a control unit.

The nozzle is preferably disposed to eject clean air from the upper stage onto the wafer surface This arrangement permits reliable protection of the wafer surface from the surrounding minute particles that might be otherwise deposited on the wafer surface.

The optical microscope preferably includes an eyepiece lens cylinder for enabling an operator to visually inspect the wafer surface as a metallurgical microscope and a change lever for switching the optical paths between the photomultiplier and the eyepiece lens cylinder. This arrangement permits the operator to visually example, if necessary, the condition of the wafer surface and see how the surface is contaminated by minute particles.

BRIEF DESCRIPTION OF THE DRAWING

The figure is a side view of an apparatus for detecting minute particles according to the invention.

DETAILED DESCRIPTION OF THE PREFERRED EMBODIMENT

Figure 1:
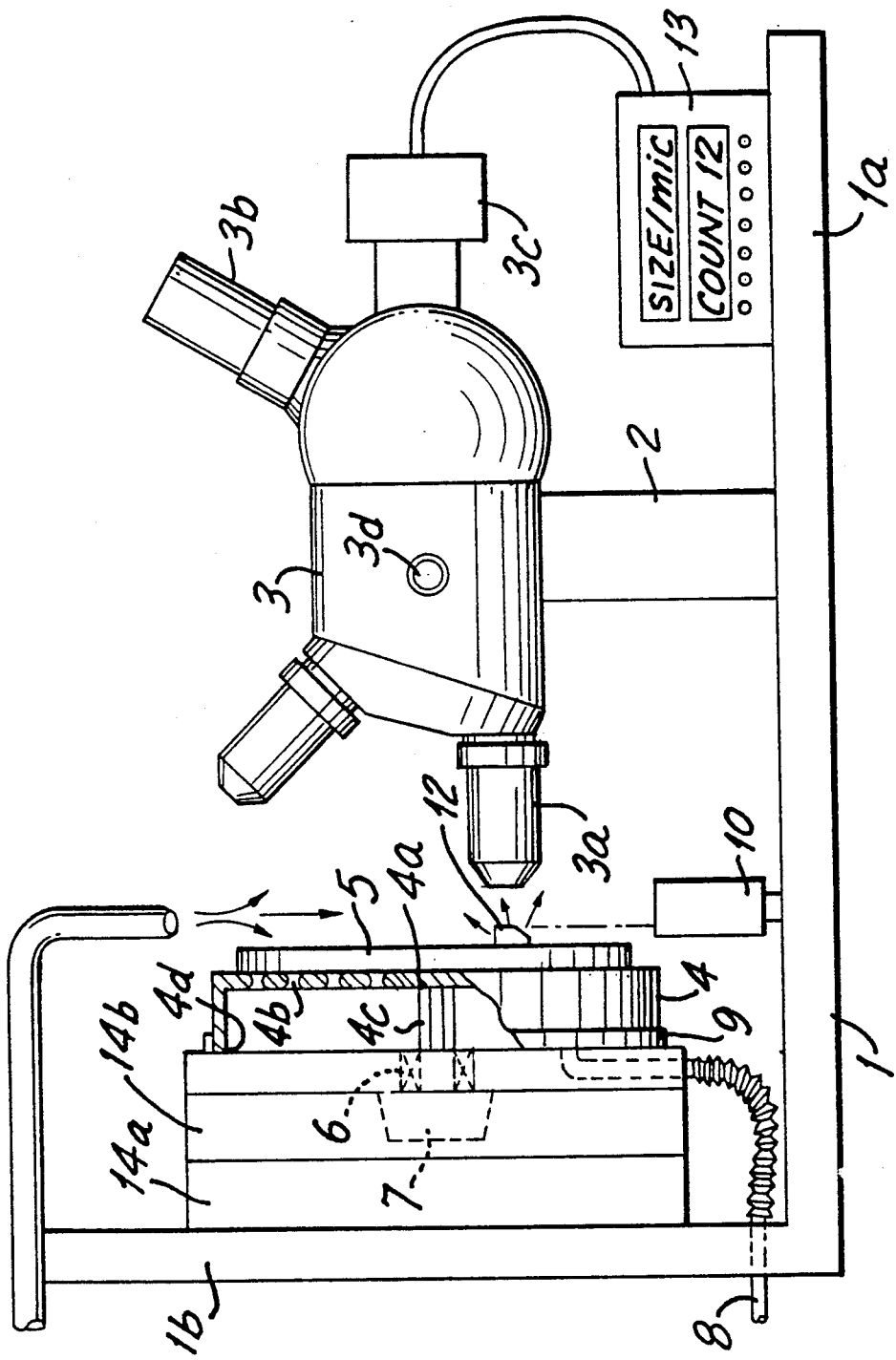

An embodiment of the present invention will now be described with reference to the figure.

As shown in the Figure, an L-shaped base 1 is composed of a horizontal portion 1a on which a vertical support 2 is mounted and vertical portion 1b. An optical microscope 3 is mounted on the support 2. The microscope 3 has a change lever 3d for selectively directing the beam of light passing through the objective lens 3a to an eyepiece lens cylinder 3b or a photomultiplier 3c. After the direction is adjusted, the change lever 3d is fastened to fix the optical microscope 3.

As shown in the figure, an X-axis stage 14a is attached on the vertical portion 1b of the L-shaped base 1. This stage 14a moves horizontally along the X-axis and is controlled by control unit 13. A Z-axis stage 14b is attached on the X-axis stage 14a. This stage 14b moves along the Z-axis and is controlled by control unit 13 too. A rotary stage 4, which is shown partially in cross section, is rotatably mounted on the Z-axis stage 14b. The rotary stage 4 is constructed in the form of a hollow cylinder having one end closed by a wall 4a and the other open and in frictional contact with the surface of the Z-axis stage 14b. The closed end wall 4a is formed with a plurality of suction holes 4b for sucking air therethrough to hold a wafer 5 on the outer surface of the wall 4a. A shaft 4c which extends from the center of the closed end wall 4a is supported by a bearing 6 buried in the Z-axis stage 14b. The shaft 4c is coupled to a drive shaft of a motor 7 burried in the Z-axis stage 14b, so that the open end 4d is rotated in frictional contact with the surface of the Z-axis stage 14b when the rotary stage 4 is rotated. The rotation degrees of the stage 4 are measured by a rotary encoder and are sent to the control unit 13.

An exhaust duct 8 is fit into the holes of the stage 14b and the vertical portion lb of the base 1. This exhaust duct 8 extracts the air trapped in the space surrounded by the inner rotary stage 4 and the surface of the stage 14b. In order to prevent leakage of ambient air through gaps between the open end 4d of the stage 4 and the surface of the stage 14b a sealing member 9 is provided around the outer peripheral portion of the open end 4d of the stage 4 and surface of the stage 14b.

A spot laser beam scanner 10 is mounted on the horizontal portion 1a of the base 1. This laser scanner 10 provides a minute spot laser beam directed to the surface of the wafer 5 held on the rotary stage 4.

An air nozzle 11 is mounted on the top of the vertical portion 1b of the base 1 for ejecting clean air from the upper stage 4 onto the stage 4 to blow off the dust and minute particles on the surface of the wafer 5 during the inspection.

The apparatuses of the present embodiment having the above construction are preferably installed at suitable wafer processing stations for forming circuits on the semiconductor wafer 5. When wafer 5 is conveyed from a preceding wafer processing station by an automatic system and set on the closed side wall 4a of the rotary stage 4 associated with the station, an evacuation unit (not shown) is operated by the control unit 13 to extract the air out of the inner space of the stage 4 through the exhaust duct 8, thereby generating a negative pressure therein, which acts on the wafer 5 through the suction holes 4b and holds the wafer 5 in position on the closed side wall 4a. Clean air is furnished from the nozzle 11 with a pressure of about 0.1 to 0.5 atmosphere (1.1-1.5 atm.) and flows downward on the surface of the wafer 5. At the same time, the surface of the wafer 5 is exposed with a minute spot laser beam from the spot laser beam scanner 10. The rotary stage 4 is rotated at a fixed speed by the motor 7 and the Z-axis stage 14b moves at fixed speed in the Z-axis, as a result, the range of the optical microscope 3 is relatively moved along the radius direction from the outer periphery towards the center of the wafer 5 scanning the whole surface of the wafer. In this case, the change lever 3d is held in the position which the reflected light from the objective lens cylinder 3a of the optical microscope 3 is routed to the photomultiplier 3c.

If minute particles 12 exist on the surface of the wafer 5, they scatter the laser beam. A part of the scattered light passes through the objective lens cylinder 3a to the photomultiplier 3c. This photomultiplier 3c is connected to the control unit 13 containing the signal processor which counts and displays the sizes and number of the particles. Thus, the minute particles 12 on the surface of the wafer 5 are detected.

Visual observation of the surface of the wafer 5 through the eyepiece lens cylinder 3b may be made, if necessary, to judge whether the wafer 5 is defective or not according to the number of minute particles 12 on the the surface of the wafer 5. Through such observations of a metallurgical microscope, it is possible to find the dirty regions on the wafer surface where deposition of particles is significant. Such survey helps the improvement of the semiconductor process quality control.

As stated above, since the wafer 5 is held vertically on the rotary stage 4 and blown downward by the clean air, and since the optical axis of the microscope 3 is held in a horizontal plane, the inspection may be carried out without the fear of dust deposition on the wafer. It should be noted that mechanical means using a chuck or the like may be alternatively used for holding a wafer on the stage.

While it is most effective to blow the surface of the wafer 5 with clean air from the upper nozzle 11 downward, it is also effective to blow the wafer 5 from a horizontal nozzle or an oblique nozzle.

It should be understood that ordinary spot light scanning source and a light sensor may equally be used in lieu of the laser scanner and the photomultiplier, respectively.

I claim:

1. An apparatus for detecting surface defects on a wafer, comprising:
    a rotary stage for holding a wafer such that a wafer surface is maintained vertically;
    a light emitter for illuminating said wafer surface;
    an optical microscope including an objective lens having an optical axis directed normal to said wafer surface maintained vertically, for receiving light reflected from said wafer surface; and
    a light sensor optically coupled to said objective lens so as to sense said light received from said wafer surface.

2. The apparatus as claimed in claim 1, further comprising a nozzle for ejecting clean air onto said wafer surface from one direction.

3. The apparatus according to claim 2, wherein said light emitter is a spot laser beam generator, and said light sensor is a photomultiplier.

4. The apparatus according to claim 3, wherein said rotary stage is rotatably supported on a Z-X stage which is supported on a vertical portion of a substantially L-shaped base, and said optical microscope is mounted on a horizontal portion of said L-shaped base.

5. The apparatus according to claim 4, wherein said rotary stage is constructed in the form of a hollow cylinder with one end thereof closed by a wall formed with a plurality of suction holes and the other end in frictional contact with a vertical surface of said Z-X stage being, said rotary stage provided with an exhaust duct for extracting air trapped in an inner space of said hollow cylinder.

6. The apparatus according to claim 5, wherein said rotary stage is rotated by a motor, and said Z-X stage is finely moved vertically.

7. The apparatus according to claim 6, wherein said nozzle is disposed above said rotary stage to eject clean air at an upper end of said rotary stage onto said wafer surface.

8. The apparatus according to claim 1, wherein said light sensor is a photomultiplier, and said optical microscope includes an eyepiece lens cylinder and a selecting means for selecting one of the photomultiplier and eyepiece lens cylinder and optically coupling a selected one of the photomultiplier and the eyepiece lens cylinder to said objective lens.

* * * * *